(12) United States Patent
Wen

(10) Patent No.: US 10,624,717 B2
(45) Date of Patent: Apr. 21, 2020

(54) TOOTH MODELING SYSTEM

(71) Applicant: uLab Systems, Inc., Menlo Park, CA (US)

(72) Inventor: Huafeng Wen, Redwood Shores, CA (US)

(73) Assignee: uLab Systems Inc., Redwood City, CA (US)

(*) Notice: Subject to any disclaimer, the term of this patent is extended or adjusted under 35 U.S.C. 154(b) by 0 days.

(21) Appl. No.: 15/230,139

(22) Filed: Aug. 5, 2016

(65) Prior Publication Data

US 2017/0100207 A1 Apr. 13, 2017

Related U.S. Application Data

(60) Provisional application No. 62/238,554, filed on Oct. 7, 2015.

(51) Int. Cl.
*A61C 7/00* (2006.01)
*A61C 9/00* (2006.01)
(Continued)

(52) U.S. Cl.
CPC ............... *A61C 7/002* (2013.01); *A61C 7/08* (2013.01); *A61C 9/00* (2013.01); *A61C 9/004* (2013.01); *G06F 30/20* (2020.01); *G06T 7/0012* (2013.01); *G06T 11/60* (2013.01); *G06T 19/20* (2013.01); *A61B 6/032* (2013.01); *A61B 6/14* (2013.01); *G06T 2207/10081* (2013.01); *G06T 2207/20036* (2013.01); *G06T 2207/30036* (2013.01); *G06T 2210/41* (2013.01); *G06T 2219/004* (2013.01); *G06T 2219/2021* (2013.01)

(58) Field of Classification Search
CPC .............. A61C 7/002; A61C 2007/004; G06T 2207/20068; G06T 2207/20096; G06T 2207/30004; G06T 2207/30036
USPC ........................................................ 433/213
See application file for complete search history.

(56) References Cited

U.S. PATENT DOCUMENTS 4,068,379 A 1/1978 Miller et al.
4,889,485 A 12/1989 Iida
(Continued)

FOREIGN PATENT DOCUMENTS

CA 2557573 7/2012
CN 1973291 9/2010
(Continued)

*Primary Examiner* — Yogesh P Patel
*Assistant Examiner* — Stephen R Sparks
(74) *Attorney, Agent, or Firm* — Levine Bagade Han LLP

(57) ABSTRACT

Systems and methods are disclosed for treating teeth to correct for malocclusions. This may be accomplished by applying a series of labels to a digital dental model and applying a rolling ball process to identify tooth boundaries separating one tooth from a neighboring tooth and to also determine the crown/gum margin. The user may further assign regions to the dental model to indicate hard regions and soft regions. With the dental model labeled and defined, the user may then generate a treatment plan for moving the labeled and defined tooth or teeth relative to one another to correct for any malocclusions. Upon approval of the treatment plan, a series of 3D printed dental appliances or aligners to be worn in series by the patient may be fabricated to ultimately move the tooth or teeth to a desired position.

22 Claims, 7 Drawing Sheets

(51) Int. Cl.
  *A61C 7/08* (2006.01)
  *G06T 7/00* (2017.01)
  *G06T 11/60* (2006.01)
  *G06T 19/20* (2011.01)
  *A61B 6/03* (2006.01)
  *A61B 6/14* (2006.01)
  *G06F 30/20* (2020.01)

(56) References Cited

U.S. PATENT DOCUMENTS

| | | | |
|---|---|---|---|
| 4,983,334 | A | 1/1991 | Adell |
| 5,055,039 | A | 10/1991 | Abbatte et al. |
| 5,186,623 | A | 2/1993 | Breads et al. |
| 5,691,905 | A | 11/1997 | Dehoff et al. |
| 5,975,893 | A | 11/1999 | Chishti et al. |
| 6,183,248 | B1 | 2/2001 | Chishti et al. |
| 6,210,162 | B1 | 4/2001 | Chishti et al. |
| 6,217,325 | B1 | 4/2001 | Chishti et al. |
| 6,227,850 | B1 | 5/2001 | Chishti et al. |
| 6,227,851 | B1 | 5/2001 | Chishti et al. |
| 6,250,918 | B1 | 6/2001 | Sachdeva et al. |
| 6,299,440 | B1 | 10/2001 | Phan et al. |
| 6,309,215 | B1 | 10/2001 | Phan et al. |
| 6,315,553 | B1 | 11/2001 | Sachdeva et al. |
| 6,386,878 | B1 | 5/2002 | Pavlovskaia et al. |
| 6,390,812 | B1 | 5/2002 | Chishti et al. |
| 6,398,548 | B1 | 6/2002 | Chishti et al. |
| 6,454,565 | B2 | 9/2002 | Phan et al. |
| 6,463,344 | B1 * | 10/2002 | Pavloskaia ............. B33Y 80/00 700/98 |
| 6,471,511 | B1 * | 10/2002 | Chishti ................. A61C 7/00 |
| 6,485,298 | B2 | 11/2002 | Chishti et al. |
| 6,488,499 | B1 | 12/2002 | Miller |
| 6,524,101 | B1 | 2/2003 | Phan et al. |
| 6,554,611 | B2 | 4/2003 | Chishti et al. |
| 6,572,372 | B1 | 6/2003 | Phan et al. |
| 6,582,227 | B2 | 6/2003 | Phan et al. |
| 6,602,070 | B2 | 8/2003 | Miller et al. |
| 6,607,382 | B1 | 8/2003 | Kuo et al. |
| 6,626,666 | B2 | 9/2003 | Chishti et al. |
| 6,629,840 | B2 | 10/2003 | Chishti et al. |
| 6,682,346 | B2 | 1/2004 | Chishti et al. |
| 6,688,885 | B1 | 2/2004 | Sachdeva et al. |
| 6,699,037 | B2 | 3/2004 | Chishti et al. |
| 6,702,575 | B2 | 3/2004 | Hilliard |
| 6,705,861 | B2 | 3/2004 | Chishti et al. |
| 6,705,863 | B2 | 3/2004 | Phan et al. |
| 6,722,880 | B2 | 4/2004 | Chishti et al. |
| 6,729,876 | B2 | 5/2004 | Chishti et al. |
| 6,761,560 | B2 | 7/2004 | Miller |
| 6,783,360 | B2 | 8/2004 | Chishti |
| 6,786,721 | B2 | 9/2004 | Chishti et al. |
| 6,802,713 | B1 | 10/2004 | Chishti et al. |
| 6,830,450 | B2 | 12/2004 | Knopp et al. |
| 6,846,179 | B2 | 1/2005 | Chapouland et al. |
| 6,857,429 | B2 | 2/2005 | Eubank |
| 6,886,566 | B2 | 5/2005 | Eubank |
| 6,964,564 | B2 | 11/2005 | Phan et al. |
| 7,011,517 | B2 | 3/2006 | Nicozisis |
| 7,029,275 | B2 | 4/2006 | Rubbert et al. |
| 7,037,108 | B2 | 5/2006 | Chishti et al. |
| 7,040,896 | B2 | 5/2006 | Pavlovskaia et al. |
| 7,056,115 | B2 | 6/2006 | Phan et al. |
| 7,059,850 | B1 | 6/2006 | Phan et al. |
| 7,063,533 | B2 | 6/2006 | Phan et al. |
| 7,074,038 | B1 | 7/2006 | Miller |
| 7,077,647 | B2 | 7/2006 | Choi et al. |
| 7,092,784 | B1 | 8/2006 | Simkins |
| 7,104,790 | B2 | 9/2006 | Cronauer |
| 7,121,825 | B2 | 10/2006 | Chishti et al. |
| 7,125,248 | B2 | 10/2006 | Phan et al. |
| 7,134,874 | B2 | 11/2006 | Chishti et al. |
| 7,156,661 | B2 | 1/2007 | Choi et al. |
| 7,160,110 | B2 | 1/2007 | Imgrund et al. |
| 7,172,417 | B2 | 2/2007 | Sporbert et al. |
| 7,192,275 | B2 | 3/2007 | Miller |
| 7,220,122 | B2 | 5/2007 | Chishti |
| 7,320,592 | B2 | 1/2008 | Chishti et al. |
| 7,326,051 | B2 | 2/2008 | Miller |
| 7,331,783 | B2 | 2/2008 | Chishti et al. |
| 7,347,688 | B2 | 3/2008 | Kopelman et al. |
| 7,416,407 | B2 | 8/2008 | Cronauer |
| 7,434,582 | B2 | 10/2008 | Eubank |
| 7,435,083 | B2 | 10/2008 | Chishti et al. |
| 7,442,041 | B2 | 10/2008 | Imgrund et al. |
| 7,458,812 | B2 | 12/2008 | Sporbert et al. |
| 7,476,100 | B2 | 1/2009 | Kuo |
| 7,553,157 | B2 | 6/2009 | Abolfathi et al. |
| 7,559,328 | B2 | 7/2009 | Eubank |
| 7,578,673 | B2 | 8/2009 | Wen et al. |
| 7,590,462 | B2 | 9/2009 | Rubbert et al. |
| 7,637,262 | B2 | 12/2009 | Bailey |
| 7,641,828 | B2 | 1/2010 | Desimone et al. |
| 7,658,610 | B2 | 2/2010 | Knopp |
| 7,689,398 | B2 | 3/2010 | Cheng et al. |
| 7,717,708 | B2 | 5/2010 | Sachdeva et al. |
| 7,771,195 | B2 | 8/2010 | Knopp et al. |
| 7,802,987 | B1 | 9/2010 | Phan et al. |
| 7,824,180 | B2 | 11/2010 | Abolfathi et al. |
| 7,826,646 | B2 * | 11/2010 | Pavlovskaia ........... A61C 7/002 382/128 |
| 7,841,858 | B2 | 11/2010 | Knopp et al. |
| 7,854,609 | B2 | 12/2010 | Chen et al. |
| 7,878,801 | B2 | 2/2011 | Abolfathi et al. |
| 7,878,804 | B2 | 2/2011 | Korytov et al. |
| 7,878,805 | B2 | 2/2011 | Moss et al. |
| 7,883,334 | B2 | 2/2011 | Li et al. |
| 7,901,207 | B2 | 3/2011 | Knopp et al. |
| 7,905,724 | B2 | 3/2011 | Kuo et al. |
| 7,914,283 | B2 | 3/2011 | Kuo |
| 7,942,672 | B2 | 5/2011 | Kuo |
| 7,943,079 | B2 | 5/2011 | Desimone et al. |
| 7,957,824 | B2 | 6/2011 | Boronvinskih et al. |
| 7,987,099 | B2 | 7/2011 | Kuo et al. |
| 8,001,972 | B2 | 8/2011 | Eubank |
| 8,021,147 | B2 | 9/2011 | Sporbert et al. |
| 8,033,282 | B2 | 10/2011 | Eubank |
| 8,038,444 | B2 | 10/2011 | Kitching et al. |
| 8,070,487 | B2 | 12/2011 | Chishti et al. |
| 8,075,306 | B2 | 12/2011 | Kitching et al. |
| 8,099,268 | B2 | 1/2012 | Kitching et al. |
| 8,099,305 | B2 | 1/2012 | Kuo et al. |
| 8,105,080 | B2 | 1/2012 | Chishti et al. |
| 8,123,519 | B2 | 2/2012 | Schultz |
| 8,152,518 | B2 | 4/2012 | Kuo |
| 8,152,523 | B2 | 4/2012 | Sporbert et al. |
| 8,235,713 | B2 | 8/2012 | Phan et al. |
| 8,272,866 | B2 | 9/2012 | Chun et al. |
| 8,275,180 | B2 | 9/2012 | Kuo et al. |
| 8,292,617 | B2 | 10/2012 | Brandt et al. |
| 8,303,302 | B2 | 11/2012 | Teasdale |
| 8,348,665 | B2 | 1/2013 | Kuo |
| 8,356,993 | B1 | 1/2013 | Marston |
| 8,401,686 | B2 | 3/2013 | Moss et al. |
| 8,401,826 | B2 | 3/2013 | Cheng et al. |
| 8,439,672 | B2 | 5/2013 | Matov et al. |
| 8,439,673 | B2 | 5/2013 | Korytov et al. |
| 8,444,412 | B2 | 5/2013 | Baughman et al. |
| 8,465,280 | B2 | 6/2013 | Sachdeva et al. |
| 8,469,705 | B2 | 6/2013 | Sachdeva et al. |
| 8,469,706 | B2 | 6/2013 | Kuo |
| 8,496,474 | B2 | 7/2013 | Chishti et al. |
| 8,512,037 | B2 | 8/2013 | Andreiko |
| 8,517,726 | B2 | 8/2013 | Kakavand et al. |
| 8,535,580 | B2 | 9/2013 | Puttler et al. |
| 8,562,337 | B2 | 10/2013 | Kuo et al. |
| 8,562,338 | B2 | 10/2013 | Kitching et al. |
| 8,562,340 | B2 | 10/2013 | Chishti et al. |
| 8,636,509 | B2 | 1/2014 | Miller |
| 8,636,510 | B2 | 1/2014 | Kitching et al. |
| 8,690,568 | B2 | 4/2014 | Chapoulaud et al. |
| 8,708,697 | B2 | 4/2014 | Li et al. |
| 8,734,149 | B2 | 5/2014 | Phan et al. |

(56) References Cited

U.S. PATENT DOCUMENTS

| | | |
|---|---|---|
| 8,734,150 B2 | 5/2014 | Chishti et al. |
| 8,738,165 B2 | 5/2014 | Cinader, Jr. et al. |
| 8,765,031 B2 | 7/2014 | Li et al. |
| 8,777,611 B2 | 7/2014 | Cios |
| 8,780,106 B2 | 7/2014 | Chishti et al. |
| 8,807,999 B2 | 8/2014 | Kuo et al. |
| 8,858,226 B2 | 10/2014 | Phan et al. |
| 8,864,493 B2 | 10/2014 | Leslie-Martin et al. |
| 8,899,976 B2 | 12/2014 | Chen et al. |
| 8,899,978 B2 | 12/2014 | Kitching et al. |
| 8,930,219 B2 | 1/2015 | Trosien et al. |
| 8,936,464 B2 | 1/2015 | Kopelman |
| 8,998,608 B2 | 1/2015 | Trosien et al. |
| 8,944,812 B2 | 2/2015 | Kuo |
| 8,961,173 B2 | 2/2015 | Miller |
| 8,986,003 B2 | 3/2015 | Valoir |
| 8,992,215 B2 | 3/2015 | Chapoulaud et al. |
| 9,004,915 B2 | 4/2015 | Moss et al. |
| 9,022,781 B2 | 5/2015 | Kuo et al. |
| 9,026,238 B2 | 5/2015 | Kraemer et al. |
| 9,060,829 B2 | 6/2015 | Sterental et al. |
| 9,107,722 B2 | 8/2015 | Matov et al. |
| 9,119,691 B2 | 9/2015 | Namiranian et al. |
| 9,161,823 B2 | 10/2015 | Morton et al. |
| 9,161,824 B2 | 10/2015 | Chishti et al. |
| 9,204,942 B2 | 12/2015 | Phan et al. |
| 9,211,166 B2 | 12/2015 | Kuo et al. |
| 9,241,774 B2 | 1/2016 | Li et al. |
| 9,301,814 B2 | 4/2016 | Kaza et al. |
| 9,320,575 B2 | 4/2016 | Chishti et al. |
| 9,326,830 B2 | 5/2016 | Kitching et al. |
| 9,326,831 B2 | 5/2016 | Cheang |
| 9,333,052 B2 | 5/2016 | Miller |
| 9,345,557 B2 | 5/2016 | Anderson et al. |
| 9,351,809 B2 | 5/2016 | Phan et al. |
| 9,364,297 B2 | 6/2016 | Kitching et al. |
| 9,375,300 B2 | 6/2016 | Matov et al. |
| 9,414,897 B2 | 8/2016 | Wu et al. |
| 9,433,476 B2 | 9/2016 | Khardekar et al. |
| 9,492,245 B2 | 11/2016 | Sherwood et al. |
| 9,844,420 B2 | 12/2017 | Cheang |
| 9,922,170 B2 | 3/2018 | Trosien et al. |
| 10,022,204 B2 | 7/2018 | Cheang |
| 10,335,250 B2 | 7/2019 | Wen |
| 10,357,336 B2 | 7/2019 | Wen |
| 10,357,342 B2 | 7/2019 | Wen |
| 2002/0010568 A1 | 1/2002 | Rubbert et al. |
| 2002/0025503 A1 | 2/2002 | Chapoulaud et al. |
| 2002/0042038 A1 | 4/2002 | Miller et al. |
| 2002/0072027 A1 | 6/2002 | Chisti |
| 2002/0094503 A1 | 7/2002 | Chishti et al. |
| 2002/0150859 A1 | 11/2002 | Imgrund et al. |
| 2002/0177108 A1 | 11/2002 | Pavlovskaia et al. |
| 2003/0008259 A1 | 1/2003 | Kuo et al. |
| 2003/0039940 A1 | 2/2003 | Miller |
| 2003/0190576 A1 | 10/2003 | Phan et al. |
| 2004/0023188 A1 | 2/2004 | Pavlovskaia et al. |
| 2004/0029068 A1 | 2/2004 | Sachdeva et al. |
| 2004/0038168 A1 | 2/2004 | Choi et al. |
| 2004/0142299 A1 | 7/2004 | Miller |
| 2004/0152036 A1 | 8/2004 | Abolfathi |
| 2004/0166456 A1 | 8/2004 | Chishti et al. |
| 2004/0166462 A1 | 8/2004 | Phan et al. |
| 2004/0166463 A1 | 8/2004 | Wen et al. |
| 2004/0197728 A1 | 10/2004 | Abolfathi et al. |
| 2004/0202983 A1 | 10/2004 | Tricca et al. |
| 2004/0242987 A1 | 12/2004 | Liew et al. |
| 2005/0010450 A1 | 1/2005 | Hultgren et al. |
| 2005/0019721 A1 | 1/2005 | Chishti |
| 2005/0048432 A1 | 3/2005 | Choi et al. |
| 2005/0095552 A1 | 5/2005 | Sporbert et al. |
| 2005/0095562 A1 | 5/2005 | Sporbert et al. |
| 2005/0118555 A1 | 6/2005 | Sporbert et al. |
| 2005/0153255 A1 | 7/2005 | Sporbert et al. |
| 2005/0192835 A1 | 9/2005 | Kuo et al. |
| 2005/0244782 A1 | 11/2005 | Chishti et al. |
| 2005/0271996 A1 | 12/2005 | Sporbert et al. |
| 2006/0003283 A1 | 1/2006 | Miller et al. |
| 2006/0035197 A1 | 2/2006 | Hishimoto |
| 2006/0068353 A1 | 3/2006 | Abolfathi et al. |
| 2006/0078840 A1 | 4/2006 | Robson |
| 2006/0078841 A1 | 4/2006 | Desimone et al. |
| 2006/0093982 A1 | 5/2006 | Wen |
| 2006/0099546 A1 | 5/2006 | Bergersen |
| 2006/0115785 A1 | 6/2006 | Li et al. |
| 2006/0147872 A1 | 7/2006 | Andreiko |
| 2006/0177789 A1 | 8/2006 | O'Bryan |
| 2006/0188834 A1 | 8/2006 | Hilliard |
| 2006/0199142 A1 | 9/2006 | Liu et al. |
| 2006/0223022 A1 | 10/2006 | Solomon |
| 2006/0223023 A1 | 10/2006 | Lai et al. |
| 2006/0275731 A1 | 12/2006 | Wen et al. |
| 2007/0003907 A1 | 1/2007 | Chishti et al. |
| 2007/0238065 A1 | 10/2007 | Sherwood et al. |
| 2007/0283967 A1 | 12/2007 | Bailey |
| 2008/0032248 A1 | 2/2008 | Kuo |
| 2008/0044786 A1 | 2/2008 | Kalili |
| 2008/0050692 A1 | 2/2008 | Hilliard |
| 2008/0051650 A1 | 2/2008 | Massie et al. |
| 2008/0057461 A1 | 3/2008 | Cheng et al. |
| 2008/0057462 A1 | 3/2008 | Kitching et al. |
| 2008/0076086 A1 | 3/2008 | Kitching et al. |
| 2008/0085487 A1 | 4/2008 | Kuo et al. |
| 2008/0118882 A1 | 5/2008 | Su |
| 2008/0141534 A1 | 6/2008 | Hilliard |
| 2008/0182220 A1* | 7/2008 | Chishti .................... A61C 7/00 433/24 |
| 2008/0206702 A1 | 8/2008 | Hedge et al. |
| 2008/0215176 A1 | 9/2008 | Borovinskih et al. |
| 2008/0248438 A1 | 10/2008 | Desimone et al. |
| 2008/0248443 A1 | 10/2008 | Chisti et al. |
| 2008/0261165 A1 | 10/2008 | Steingart et al. |
| 2008/0268400 A1 | 10/2008 | Moss et al. |
| 2008/0280247 A1 | 11/2008 | Sachdeva et al. |
| 2008/0305451 A1 | 12/2008 | Kitching et al. |
| 2008/0305453 A1 | 12/2008 | Kitching et al. |
| 2009/0081604 A1 | 3/2009 | Fisher |
| 2009/0191502 A1 | 7/2009 | Cao et al. |
| 2009/0269714 A1 | 10/2009 | Knopp |
| 2009/0280450 A1 | 11/2009 | Kuo |
| 2009/0291407 A1 | 11/2009 | Kuo |
| 2009/0291408 A1 | 11/2009 | Stone-Collonge et al. |
| 2010/0036682 A1 | 2/2010 | Trosien et al. |
| 2010/0055635 A1 | 3/2010 | Kakavand |
| 2010/0167225 A1 | 7/2010 | Kuo |
| 2010/0179789 A1 | 7/2010 | Sachdeva et al. |
| 2010/0280798 A1 | 11/2010 | Pattijn et al. |
| 2011/0005527 A1 | 1/2011 | Andrew et al. |
| 2011/0015591 A1 | 1/2011 | Hanson et al. |
| 2011/0020761 A1 | 1/2011 | Kalili |
| 2011/0039223 A1 | 2/2011 | Li et al. |
| 2011/0114100 A1 | 5/2011 | Alvarez et al. |
| 2011/0123944 A1 | 5/2011 | Knopp et al. |
| 2011/0129786 A1 | 6/2011 | Chun et al. |
| 2011/0165533 A1 | 7/2011 | Li et al. |
| 2011/0269092 A1 | 11/2011 | Kuo et al. |
| 2011/0269097 A1 | 11/2011 | Sporbert et al. |
| 2011/0270588 A1 | 11/2011 | Kuo et al. |
| 2011/0281229 A1 | 11/2011 | Abolfathi |
| 2012/0035901 A1 | 2/2012 | Kitching et al. |
| 2012/0123577 A1 | 5/2012 | Chapoulaud et al. |
| 2012/0150494 A1 | 6/2012 | Anderson et al. |
| 2012/0186589 A1 | 7/2012 | Singh |
| 2012/0199136 A1 | 8/2012 | Urbano |
| 2012/0214121 A1 | 8/2012 | Greenberg |
| 2012/0225399 A1 | 9/2012 | Teasdale |
| 2012/0225400 A1 | 9/2012 | Chishti et al. |
| 2012/0225401 A1 | 9/2012 | Kitching et al. |
| 2012/0244488 A1 | 9/2012 | Chishti et al. |
| 2012/0270173 A1 | 10/2012 | Pumphrey et al. |
| 2012/0288818 A1 | 11/2012 | Vendittelli |
| 2013/0022255 A1* | 1/2013 | Chen ....................... G06K 9/34 382/131 |
| 2013/0052625 A1 | 2/2013 | Wagner |

(56) References Cited

U.S. PATENT DOCUMENTS

| | | |
|---|---|---|
| 2013/0078593 A1 | 3/2013 | Andreiko |
| 2013/0081271 A1 | 4/2013 | Farzin-Nia et al. |
| 2013/0085018 A1* | 4/2013 | Jensen .................. A63B 57/00 473/404 |
| 2013/0095446 A1 | 4/2013 | Andreiko et al. |
| 2013/0122445 A1 | 5/2013 | Marston |
| 2013/0122448 A1 | 5/2013 | Kitching |
| 2013/0157213 A1 | 6/2013 | Arruda |
| 2013/0201450 A1* | 8/2013 | Bailey ..................... A61B 3/14 351/206 |
| 2013/0204583 A1 | 8/2013 | Matov et al. |
| 2013/0230819 A1 | 9/2013 | Arruda |
| 2013/0231899 A1 | 9/2013 | Khardekar et al. |
| 2013/0236848 A1 | 9/2013 | Arruda |
| 2013/0266906 A1 | 10/2013 | Soo |
| 2013/0302742 A1 | 11/2013 | Li et al. |
| 2013/0308846 A1* | 11/2013 | Chen .................... G06T 7/0012 382/131 |
| 2013/0317800 A1 | 11/2013 | Wu et al. |
| 2013/0323665 A1 | 12/2013 | Dinh et al. |
| 2013/0325431 A1* | 12/2013 | See ........................ A61C 7/002 703/11 |
| 2014/0023980 A1 | 1/2014 | Kitching et al. |
| 2014/0067335 A1 | 3/2014 | Andreiko et al. |
| 2014/0072926 A1 | 3/2014 | Valoir |
| 2014/0076332 A1 | 3/2014 | Luco |
| 2014/0124968 A1 | 5/2014 | Kim |
| 2014/0172375 A1 | 6/2014 | Grove |
| 2014/0193765 A1 | 7/2014 | Kitching et al. |
| 2014/0193767 A1 | 7/2014 | Li et al. |
| 2014/0229878 A1 | 8/2014 | Wen et al. |
| 2014/0242532 A1 | 8/2014 | Arruda |
| 2014/0272757 A1 | 9/2014 | Chishti |
| 2014/0287376 A1 | 9/2014 | Hultgren et al. |
| 2014/0288894 A1 | 9/2014 | Chishti et al. |
| 2014/0315153 A1 | 10/2014 | Kitching |
| 2014/0315154 A1 | 10/2014 | Jung et al. |
| 2014/0329194 A1 | 11/2014 | Sachdeva et al. |
| 2014/0349242 A1 | 11/2014 | Phan et al. |
| 2014/0363779 A1 | 12/2014 | Kopelman |
| 2014/0370452 A1 | 12/2014 | Tseng |
| 2015/0004553 A1 | 1/2015 | Li et al. |
| 2015/0004554 A1 | 1/2015 | Cao et al. |
| 2015/0018956 A1 | 1/2015 | Steinmann et al. |
| 2015/0025907 A1 | 1/2015 | Trosien et al. |
| 2015/0044623 A1 | 2/2015 | Rundlett |
| 2015/0044627 A1 | 2/2015 | German |
| 2015/0093713 A1 | 4/2015 | Chen et al. |
| 2015/0093714 A1 | 4/2015 | Kopelman |
| 2015/0125802 A1 | 5/2015 | Tal |
| 2015/0128421 A1 | 5/2015 | Mason et al. |
| 2015/0157421 A1 | 6/2015 | Martz et al. |
| 2015/0182321 A1 | 7/2015 | Karazivan et al. |
| 2015/0216626 A1 | 8/2015 | Ranjbar |
| 2015/0216627 A1 | 8/2015 | Kopelman |
| 2015/0238282 A1 | 8/2015 | Kuo et al. |
| 2015/0238283 A1 | 8/2015 | Tanugula et al. |
| 2015/0238284 A1 | 8/2015 | Wu et al. |
| 2015/0245887 A1 | 9/2015 | Izugami et al. |
| 2015/0254410 A1 | 9/2015 | Sterental et al. |
| 2015/0265376 A1 | 9/2015 | Kopelman |
| 2015/0289949 A1 | 10/2015 | Moss et al. |
| 2015/0289950 A1 | 10/2015 | Khan |
| 2015/0305830 A1 | 10/2015 | Howard et al. |
| 2015/0320518 A1 | 11/2015 | Namiranian et al. |
| 2015/0320532 A1 | 11/2015 | Matty et al. |
| 2015/0335399 A1 | 11/2015 | Caraballo |
| 2015/0335404 A1 | 11/2015 | Webber et al. |
| 2015/0336299 A1 | 11/2015 | Tanugula et al. |
| 2015/0342464 A1 | 12/2015 | Wundrak et al. |
| 2015/0351871 A1 | 12/2015 | Chishti et al. |
| 2015/0359609 A1 | 12/2015 | Khan |
| 2015/0366637 A1 | 12/2015 | Kopelman et al. |
| 2015/0366638 A1 | 12/2015 | Kopelman et al. |
| 2016/0000527 A1 | 1/2016 | Arruda |
| 2016/0008095 A1 | 1/2016 | Matov et al. |
| 2016/0008097 A1 | 1/2016 | Chen et al. |
| 2016/0051341 A1 | 2/2016 | Webber |
| 2016/0051342 A1 | 2/2016 | Phan et al. |
| 2016/0051348 A1 | 2/2016 | Boerjes et al. |
| 2016/0067013 A1 | 3/2016 | Morton et al. |
| 2016/0067014 A1 | 3/2016 | Kottemann et al. |
| 2016/0074137 A1 | 3/2016 | Kuo et al. |
| 2016/0074138 A1 | 3/2016 | Kitching et al. |
| 2016/0095668 A1 | 4/2016 | Kuo et al. |
| 2016/0106521 A1 | 4/2016 | Tanugula et al. |
| 2016/0120617 A1 | 5/2016 | Lee |
| 2016/0120621 A1 | 5/2016 | Li et al. |
| 2016/0128803 A1 | 5/2016 | Webber et al. |
| 2016/0135924 A1 | 5/2016 | Choi et al. |
| 2016/0135926 A1 | 5/2016 | Djamchidi |
| 2016/0135927 A1 | 5/2016 | Boltunov et al. |
| 2016/0157961 A1 | 6/2016 | Lee |
| 2016/0175068 A1 | 6/2016 | Cai et al. |
| 2016/0175069 A1 | 6/2016 | Korytov et al. |
| 2016/0184129 A1 | 6/2016 | Liptak et al. |
| 2016/0193014 A1 | 7/2016 | Morton et al. |
| 2016/0203604 A1* | 7/2016 | Gupta ..................... G06K 9/52 382/128 |
| 2016/0206402 A1 | 7/2016 | Kitching et al. |
| 2016/0256240 A1 | 9/2016 | Shivapuja et al. |
| 2016/0338799 A1 | 11/2016 | Wu et al. |
| 2016/0367339 A1 | 12/2016 | Khardekar et al. |
| 2017/0100208 A1 | 4/2017 | Wen |
| 2017/0100209 A1 | 4/2017 | Wen |
| 2017/0100210 A1 | 4/2017 | Wen |
| 2017/0100211 A1 | 4/2017 | Wen |
| 2017/0100214 A1 | 4/2017 | Wen |
| 2018/0014912 A1 | 1/2018 | Radmand |
| 2018/0078335 A1 | 3/2018 | Falkel |
| 2018/0078343 A1 | 3/2018 | Falkel |
| 2018/0078344 A1 | 3/2018 | Falkel |
| 2018/0078347 A1 | 3/2018 | Falkel |
| 2018/0092714 A1 | 4/2018 | Kitching et al. |
| 2018/0092715 A1 | 4/2018 | Kitching et al. |
| 2018/0158544 A1 | 6/2018 | Trosien et al. |
| 2018/0168781 A1 | 6/2018 | Kopelman et al. |
| 2019/0008612 A1 | 1/2019 | Kitching et al. |

FOREIGN PATENT DOCUMENTS

| | | |
|---|---|---|
| CN | 101528152 | 12/2012 |
| CN | 103932807 | 7/2014 |
| EP | 1474062 | 4/2011 |
| EP | 2056734 | 9/2015 |
| JP | 2005-515826 | 6/2005 |
| JP | 2006-500999 | 1/2006 |
| JP | 2009-202031 | 9/2009 |
| JP | 4323322 | 9/2009 |
| JP | 2010-502246 | 1/2010 |
| JP | 4566746 | 10/2010 |
| JP | 2012-139540 | 7/2012 |
| JP | 5015197 | 8/2012 |
| JP | 5015765 | 8/2012 |
| JP | 5149898 | 2/2013 |
| JP | 5291218 | 9/2013 |
| JP | 2007-525289 | 9/2017 |
| KR | 10-1450866 | 10/2014 |
| WO | WO 2001/082192 | 11/2001 |
| WO | WO 2002/047571 | 6/2002 |
| WO | WO 2003/063721 | 8/2003 |
| WO | WO 2004/028391 | 4/2004 |
| WO | WO 2005/086058 | 9/2005 |
| WO | WO 2004/098379 | 11/2005 |
| WO | WO 2006/050452 | 5/2006 |
| WO | WO 2006/096558 | 9/2006 |
| WO | WO 2008/026064 | 3/2008 |
| WO | WO 2008/149222 | 12/2008 |
| WO | WO 2009/068892 | 6/2009 |
| WO | WO 2016/004415 | 1/2016 |
| WO | WO 2017/062207 | 4/2017 |
| WO | WO 2017/062208 | 4/2017 |
| WO | WO 2017/062209 | 4/2017 |

(56) References Cited

FOREIGN PATENT DOCUMENTS

| WO | WO 2017/062210 | 4/2017 |
|----|----------------|--------|
| WO | WO 2018/057622 | 3/2018 |
| WO | WO 2018/118200 | 6/2018 |

* cited by examiner

TOOTH MODELING SYSTEM

CROSS-REFERENCE TO RELATED APPLICATIONS

This application claims the benefit of priority to U.S. Provisional Application No. 62/238,554 filed Oct. 7, 2015, which is incorporated herein by reference in its entirety.

FIELD OF THE INVENTION

The present invention relates to methods and apparatus for computerized orthodontics. More particularly, the present invention relates to methods and apparatus for planning orthodontic treatments.

BACKGROUND OF THE INVENTION

Orthodontics is a specialty of dentistry that is concerned with the study and treatment of malocclusions which can result from tooth irregularities, disproportionate facial skeleton relationships, or both. Orthodontics treats malocclusion through the displacement of teeth via bony remodeling and control and modification of facial growth.

This process has been traditionally accomplished by using static mechanical force to induce bone remodeling, thereby enabling teeth to move. In this approach, braces having an archwire interface with brackets are affixed to each tooth. As the teeth respond to the pressure applied via the archwire by shifting their positions, the wires are again tightened to apply additional pressure. This widely accepted approach to treating malocclusions takes about twenty-four months on average to complete, and is used to treat a number of different classifications of clinical malocclusion. Treatment with braces is complicated by the fact that it is uncomfortable and/or painful for patients, and the orthodontic appliances are perceived as unaesthetic, all of which creates considerable resistance to use. Further, the treatment time cannot be shortened by increasing the force, because too high a force results in root resorption, as well as being more painful. The average treatment time of twenty-four months is very long, and further reduces usage. In fact, some estimates provide that less than half of the patients who could benefit from such treatment elect to pursue orthodontics.

Kesling introduced the tooth positioning appliance in 1945 as a method of refining the final stage of orthodontic finishing after removal of the braces (debanding). The positioner was a one-piece pliable rubber appliance fabricated on the idealized wax set-ups for patients whose basic treatment was complete. Kesling also predicted that certain major tooth movements could also be accomplished with a series of positioners fabricated from sequential tooth movements on the set-up as the treatment progressed. However, this idea did not become practical until the advent of three-dimensional (3D) scanning and use of computers by companies including Align Technologies and as well as OrthoClear, ClearAligner, and ClearCorrect to provide greatly improved aesthetics since the devices are transparent.

However for traditional trim model to individual tooth, the gum geometry is lost and the fake gum is recreated, often remodeled by a technician. Hence, the gum geometry may not be accurate at first and an animation of gum changes over time due to lack of a physical model is even harder to model. Such inaccurate modeling causes the resulting aligner to be mismatched resulting in devices which are too large or too small resulting in patient discomfort.

Another problem is that without the real gum as the reference, some so-called modeled treatments cannot be achieved in reality resulting in potential errors, e.g., a tooth movement can occur within a mis-modeled gingival, however, the tooth movement may actually be moved exteriorly of a patient's real gingival.

Another problem of trimming and hole filling and creating an individual tooth and gum model is there is little information that can define the real boundary of two teeth. Such trim and fill models force the boundary surfaces to be defined even if they are arbitrary.

Depending on what boundary surface is defined, the movement can be restricted or relax, meaning some real life movement can be achieved; however, due to such inaccuracies, the modeling software is unable to model accurately due to models colliding into each other. This may cause the real treatment outcome to create gaps between teeth and further requiring final refinements which increase cost and patient dissatisfaction. On the other hand, if the modeled movement is relax, the software may enable movements which are physically impossible in reality and this may cause the modeled device to push teeth into one another unable to move. This may also cause the plastic shell of the aligner to sometimes stretch so much that the shell applies an uncomfortable amount of force, which could be painful, to a patient.

Another problem of trim and hole fill is the filling of the geometry like a real tooth, for below, the below lines are likely of boundary surfaces modeled, such models look like a real tooth; however, such sharp boundaries cause deeper undercuts which, once printed and thermal formed to have a plastic shell, make removal of the plastic shell from the printed model difficult due to the deep undercuts. To compensate for this, a bevel object is typically created to fill the clevis increasing inaccuracy and costs.

Another problem of trim and hole filling is the model size is too large to communicate between the user and manufacturer thus requiring that the model size be reduced resulting in missing model details. These inaccuracies could misguide professionals, e.g., the full complex model may not show a gap between two adjacent teeth however the reduced model may show one.

These 3D scanning and computerized planning treatments are cumbersome and time consuming. Accordingly, there exists a need for an efficient and cost effective procedure for planning the orthodontic treatment of a patient.

SUMMARY OF THE INVENTION

Systems and methods are disclosed for treating teeth to correct for malocclusions. This may be accomplished by applying a series of labels to a digital dental model and applying a rolling ball process to identify tooth boundaries separating one tooth from a neighboring tooth. The rolling ball process may also be used to determine the crown/gum margin. The user may further assign regions to the dental model to indicate hard regions (hard regions have a criteria where they cannot change their shape) and soft regions (soft regions have a criteria where they can deform with an attached hard region). With the dental model labeled and defined, the user may then generate a treatment plan for moving the labeled and defined tooth or teeth relative to one another to correct for any malocclusions. Upon approval of the treatment plan, a series of 3D printed dental appliances or aligners to be worn in series by the patient may be fabricated to ultimately move the tooth or teeth to a desired position.

One method for planning a treatment for correcting malocclusions may generally comprise receiving a scanned dental model of a subject's dentition and then applying a label to one or more teeth within the dental model. The rolling ball process may be simulated along an exterior of the one or more teeth and gums within the dental model for determining a boundary between each of the one or more teeth and gums based on a path or trajectory of the rolling ball process. The hard or soft regions may be assigned to each of the one or more teeth and gums within the dental model and a position of the one or more teeth within the dental model may be moved by the user to correct for malocclusions in developing a treatment plan. Once approved (e.g., by the patient and/or user), one or more prostheses or aligners may be fabricated to move the one or more teeth according to the treatment plan.

Moving a position of the one or more teeth in developing the treatment plan generally comprises morphing a new dental model from the dental model. As described, the one or more prostheses or aligners may be fabricated, e.g., via 3D printing the one or more aligners, so that the entire process of may be accomplished in a single visit by the subject to a dental office.

In another example for planning a treatment for correcting malocclusions, the method may generally comprise directly scanning a subject's dentition to create a digitized dental model and having the user apply a label to one or more teeth within the dental model. The simulated ball may be rolled digitally along an exterior of the one or more teeth and gums within the dental model for determining a boundary between each of the one or more teeth and gums based on a path or trajectory of the rolling ball process. The hard region may be assigned to each of the one or more teeth and a soft region may be similarly assigned to gums within the dental model. Then a position of the one or more teeth may be moved within the dental model to correct for malocclusions in developing a treatment plan.

As described, once the treatment plan has been approved (e.g., by the patient and/or user), one or more prostheses or aligners may be fabricated to move the one or more teeth according to the treatment plan and the entire process of may be accomplished in a single visit by the subject to a dental office.

Advantages of the system may include one or more of the following. The system allows close control by the treating professional at each stage by allowing specific movements from one stage to the next stage. In one example, it is desirable in some settings to synchronize the movement and operation of the individual tooth models to have a few tooth models operate in a choreographed manner as dictated by a treating professional. Having this choreographed movement is not typically possible through manual control where the tooth models move randomly and independently. The present control method and/or system are ideal for use in moving a number of tooth models and to provide synchronized tooth movement. Such a method may be non-swarming to avoid any collisions between the teeth and to also avoid the appearance of merely random movements, at least in some applications. Rather, it is desirable for the tooth models to each react safely to environmental conditions such as changes in bone structure and soft tissue during group tooth movement of choreographed tooth models.

DETAILED DESCRIPTION OF THE INVENTION

Figure 1A:
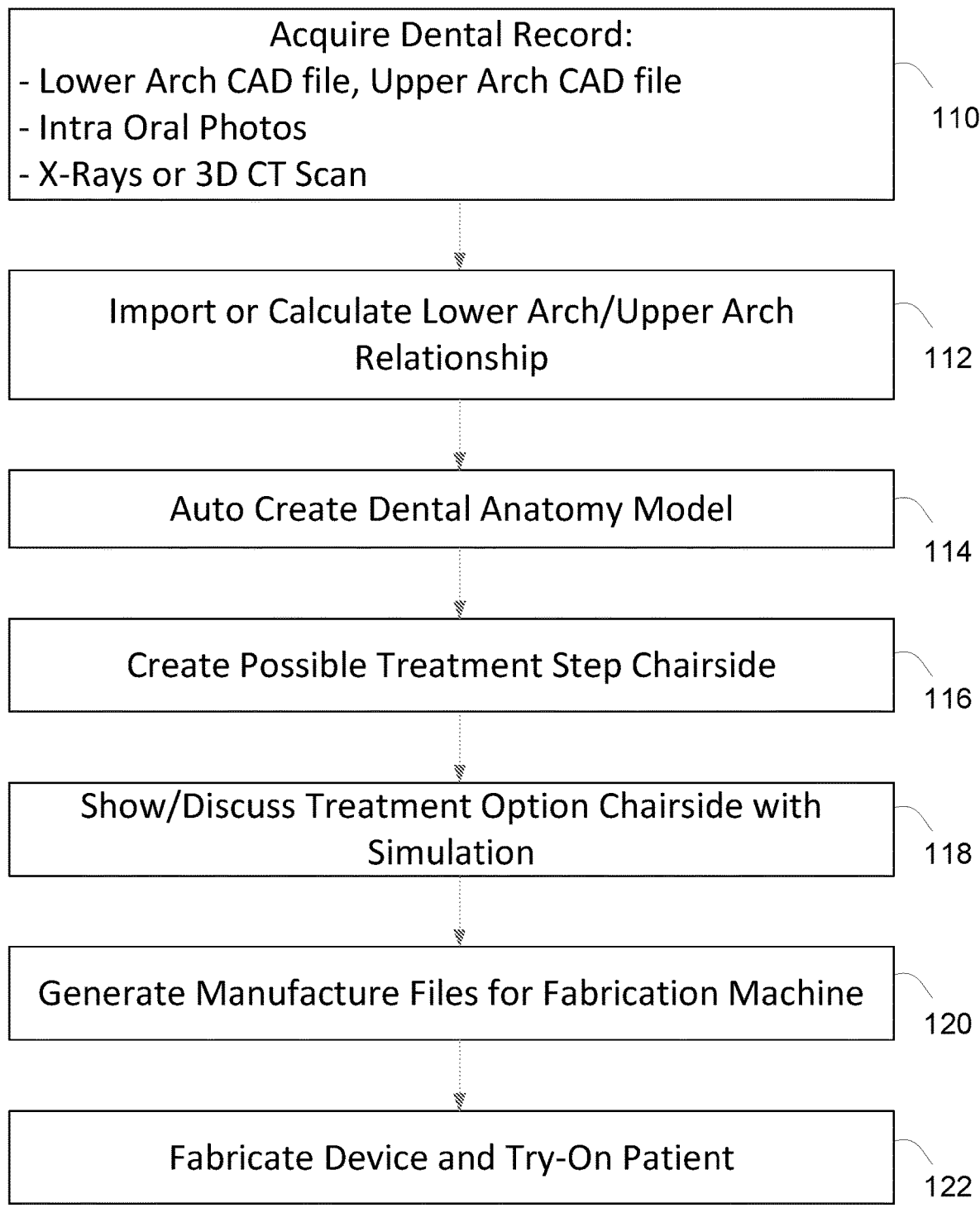
FIG. 1A shows a flow diagram of one exemplary method for a tooth modeling system.

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The treatment planning process may be implemented after receiving and analyzing the scanned dental model of a patient's dentition. The scanned dental model may be accordingly processed to enable the development of a treatment plan which can be readily implemented for fabricating one or more positioners for use in effecting sequential tooth movements.

FIG. 1A shows an exemplary overall tooth modeling process which may be used in planning the treatment for correcting malocclusions in a patient. The process shown may involve initially acquiring a patient's dental record 110 in the form of e.g., lower arch and/or upper arch CAD files, intra oral photos, X-rays or 3D CT scans, etc. The lower arch and/or upper arch CAD files may be created, for instance, through a number of different methods, such as taking lower and upper impressions of the patient's dentition, X-rays, etc.

Once the dental records are acquired, the lower arch and upper arch relationship may be imparted or calculated 112 for registration by one or more computing devices and a flexible dental anatomy model may be auto created 114 by one or more processors located locally in proximity to where the patient is treated, e.g., dental office, or remotely from the patient location. Once the dental anatomy model has been digitally created and confirmed to fit and that the arch model can open and close as expected, one or more possible treatments may be created in real-time chairside of the patient 116 and the one or more treatment options may be shown and/or discussed with the patient chairside 118 where simulations of the treatment options may also be shown and/or discussed for potentially altering the treatment plan as needed. The simulations of treatment options may be displayed to the patient using any number of electronic display methods.

Following the discussion of the treatment options with the patient, the treatment plan (with any alterations) may be used to generate manufacturing files for the fabrication machinery 120, e.g., 3D printing machines, thermal forming, laser sintering, etc. Because the resulting one or more positioners may be fabricated locally in proximity to the patient (e.g., dental office, clinic, nearby facility, etc.) the one or more resulting positioners for use by the patient may be fabricated locally allowing for the patient to try on the one or more positioners 122 during the same visit.

Such a treatment plan may have particular advantages over conventional planning and treatment plans including one or more of the following:

exact treatment may be developed right way and discussed with the patient in real time;
practitioner has full control of the treatment plan options which are easy to create;
real gum modeling may be implemented;
one or more positioners may be fabricated locally allowing the patient to try-on during the same visit;
easy to incorporate other treatment methods, e.g. indirect bonding bracket, rubber bands, hooks, retainers, etc. in combination with one or more positioners.

Figure 1B:
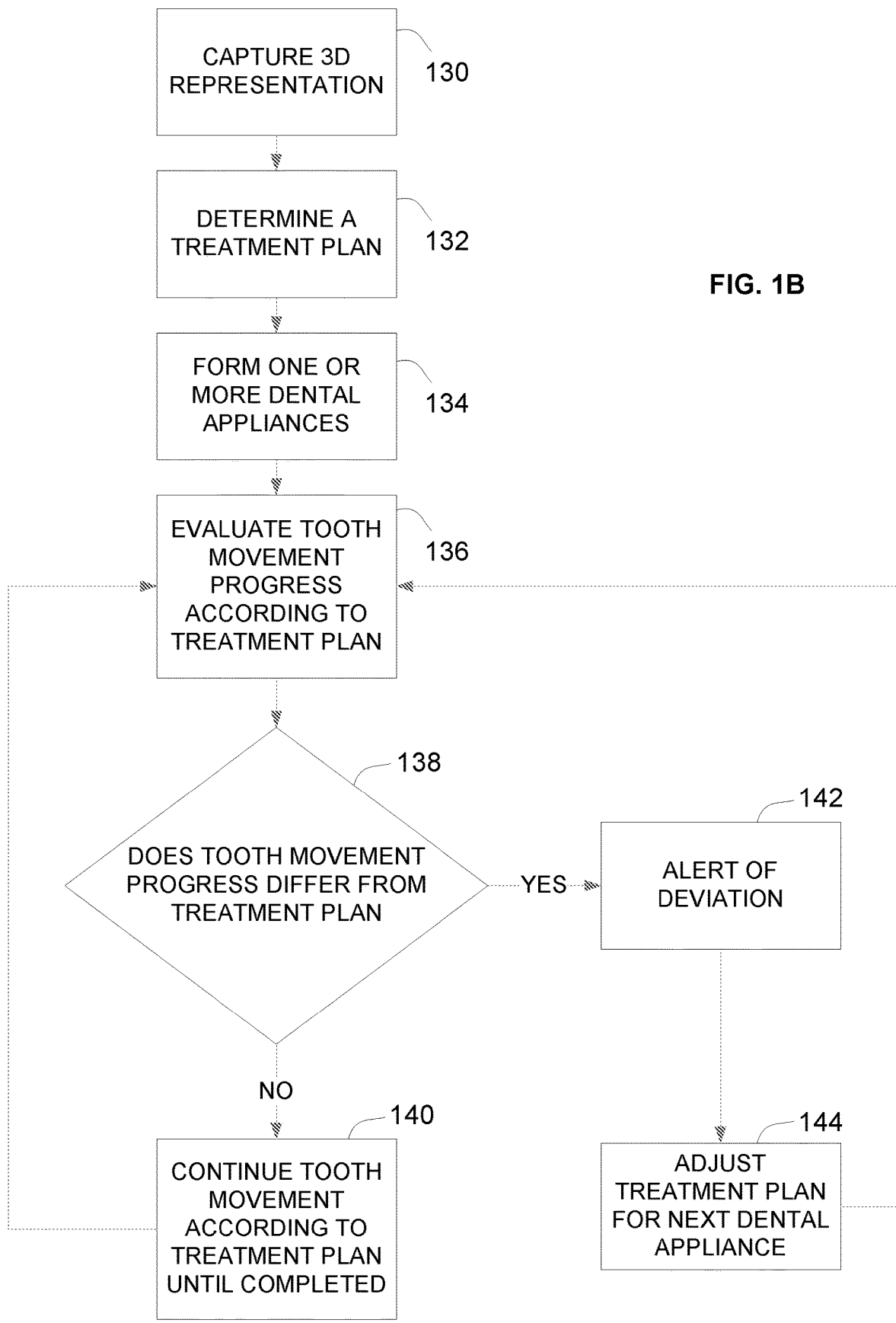
FIG. 1B shows another exemplary method for adjusting a treatment process when results deviate from the initial treatment plan.

Even in the event that a treatment plan has been developed and implemented for a patient, as shown and described for FIG. 1A, the actual progress of the tooth movement(s) may not correspond to the treatment plan or the actual progress may begin to deviate from the treatment plan. Because of this variability, not all of the positioners or aligners may be fabricated at the start of the treatment but the positioners may instead be fabricated in preset stages for use by the patient until a subsequent visit to the practitioner, e.g., every six weeks, where a new set of positioners may be fabricated for subsequent treatments. FIG. 1B shows an example of this staged treatment planning where the treatment plan may be adjusted during the actual treatment according to any changes or deviations by the patient's progress. Furthermore, the implementation of a staged treatment planning process also enables the practitioner to employ other devices or methods (e.g., brackets, wires, etc.) for correcting malocclusions in addition to or in place of the fabricated positioners.

As described above, the patient's dentition may be scanned or otherwise recorded to capture a three-dimensional (3D) representation 130 of the patient's dentition and an initial treatment plan may be determined 132 for forming one or more dental appliances 134 for correcting any malocclusions. Rather than fabricating the dental appliances for the entire treatment process, a staged number of appliances may be initially fabricated for use by the patient until their subsequent visit. The practitioner may evaluate the patient's tooth movement progress at subsequent visits according to the treatment plan 136 as originally developed. In determining whether the patient's tooth movement progress differs from the treatment plan 138, the practitioner may compare the treatment plan with the patient's actual tooth movement(s) to determine whether they correlate with one another. Such a comparison may be done in a number of ways, e.g., visually by the practitioner or the patient's dentition may be scanned again and the captured 3D representation of the treated dentition may be digitally compared against the treatment plan.

If the system determines that the actual tooth movement progress does not differ from the treatment plan, the tooth movement may be continued according to the treatment plan 140 without alteration and an additional number of positioners may be fabricated for use by the patient until the subsequent visit. Provided that the next visit and subsequent visit tracks according to the original treatment plan, the additional set of positioners may be fabricated until the treatment has been completed and the malocclusions corrected.

However, if during any one of the evaluations the practitioner determines that the actual tooth movement does differ from the treatment plan, the practitioner may be alerted of the deviation 142 by the system. The treatment plan may then be automatically adjusted by the system for the next set of dental appliances or positioners 144 to correct for the deviations so that the newly fabricated positioners provide for a better fit to the patient's dentition and is responsive to correcting for the deviations. At subsequent visits, the tooth movement with the altered treatment plan may be evaluated 136 to determine whether the tooth movement differs from the altered treatment plan 138 and if no deviation is detected, treatment may be continued but if a deviation is detected, the practitioner may be alerted of the deviation and the altered treatment plan again be adjusted accordingly. This process may be continued until the detected tooth movements appear to follow the treatment plans.

Because the system is programmed to alert the practitioner of any deviations for particular teeth, the practitioner is able to determine if the patient is non-compliant with wearing the positioner and/or whether any there are any problematic tooth movements which the practitioner can then flag for continuing treatment or whether other devices or methods, e.g., conventional braces, may be employed for particularly problematic teeth. The treatment plan (as any subsequent treatment plans) may be shared with others through any number of methods and/or devices.

Figure 2:
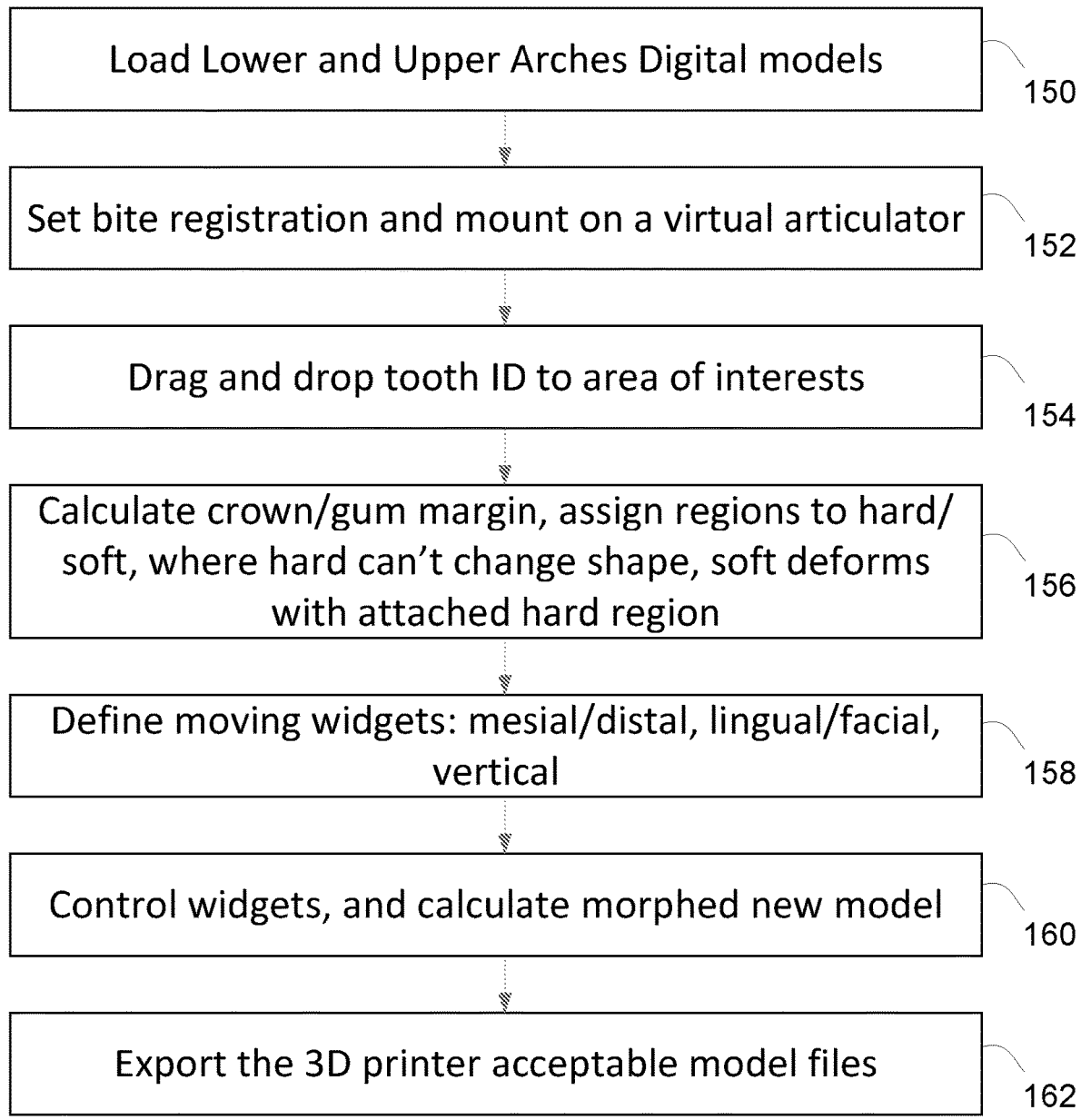
FIG. 2 shows one exemplary process for planning a treatment process in creating a model file.

In importing or calculating the relationship between the lower arch and upper arch 112, the digital models of the lower arch and/or upper arch may be loaded 150, e.g., into a computer, as shown in the flow diagram of FIG. 2. Additionally, as part of creating a dental anatomy model 114, the bite registration between the lower arch and upper arch may be set and mounted on a virtual articulator 152 and the user may then drag and drop the tooth ID to an area of interest 154 for correcting the malocclusion. In digitally modeling the margin between the crown and gum, the process may assign regions that are designated as "hard" and "soft" 156 with conditions set where a region with a "hard" designation cannot change its shape and a region with a "soft" designation is able to be deformed with an attached "hard" region.

Additionally, any number of moving widgets may be defined at various regions or locations 158 for facilitating the movement and control of the regions. For instance, the process may allow for defining moving widgets: mesial/distal, lingual/facial, vertical, etc. Moreover, the user may be enabled to control the widgets and calculate a morphed new model 160 in developing a treatment plan. Once the treatment plan has been completed, the plan may be exported, e.g., to a 3D printer acceptable model file 162, for use in manufacturing one or more of the positioners or for manufacturing molds for subsequent thermal forming.

Figure 3:
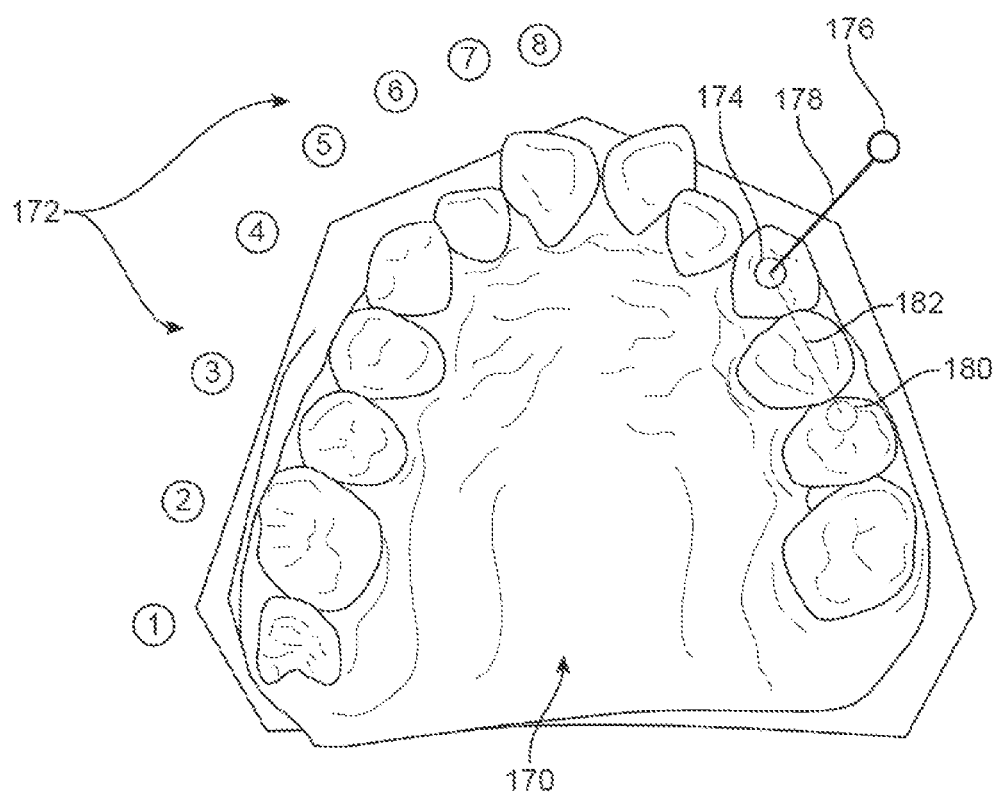
FIG. 3 shows one exemplary labeling system in planning the treatment process.

In preparing the scanned image of the patient's dentition for treatment planning, the digital model may be initially labeled. For example, FIG. 3 shows an example of a labeling system where the scanned dentition model 170 may be seen. A number of labels 172, in this example a total of 16 labels (e.g., 1 to 16 or 17-32 depending on the arch), may be initially laid out alongside the model 170 allowing for the user to assign a label to a targeted tooth by, e.g., dragging and dropping a label to a particular tooth. In this example, while the label is dragged it may remain visible but after being assigned by being dropped upon a particular tooth, the tooth may change to indicate that it has been labeled. For instance, the tooth may be changed in color to indicate that it is now labeled, e.g., from the color red to indicate an unassigned tooth to the color white to indicate the tooth being labeled.

In facilitating the treatment planning, moving widgets may be defined on the digital model 158 and controlled 160 accordingly, as discussed above. As shown in FIG. 3, one example is illustrated of a moving widget where a center vertex 174 indicated as a circle may be defined along the model 170. The selected vertex related mesh should be form a single connected region to provide a way to read the list. The center vertex 174 is indicated as a center while a second vertex 176 may be defined relative to the center vertex 174 such that the first arm 178 defined between may point directly outside the tooth surface in the lingual to buccal direction. A third vertex 180 may be defined relative to the center vertex 174 such that the second arm 182 defined between points along the center of the teeth in the mesial to distal direction. The first arm 178 and second arm 182 need not be perpendicular to one another. The moving widget may be applied only to teeth which are labeled (and hence teeth which may be moved in the model) and may provide a way to read and orient the direction of the arms 178, 182 and their origin. The moving widget may be hidden from view from the user when not in use.

Figure 4:
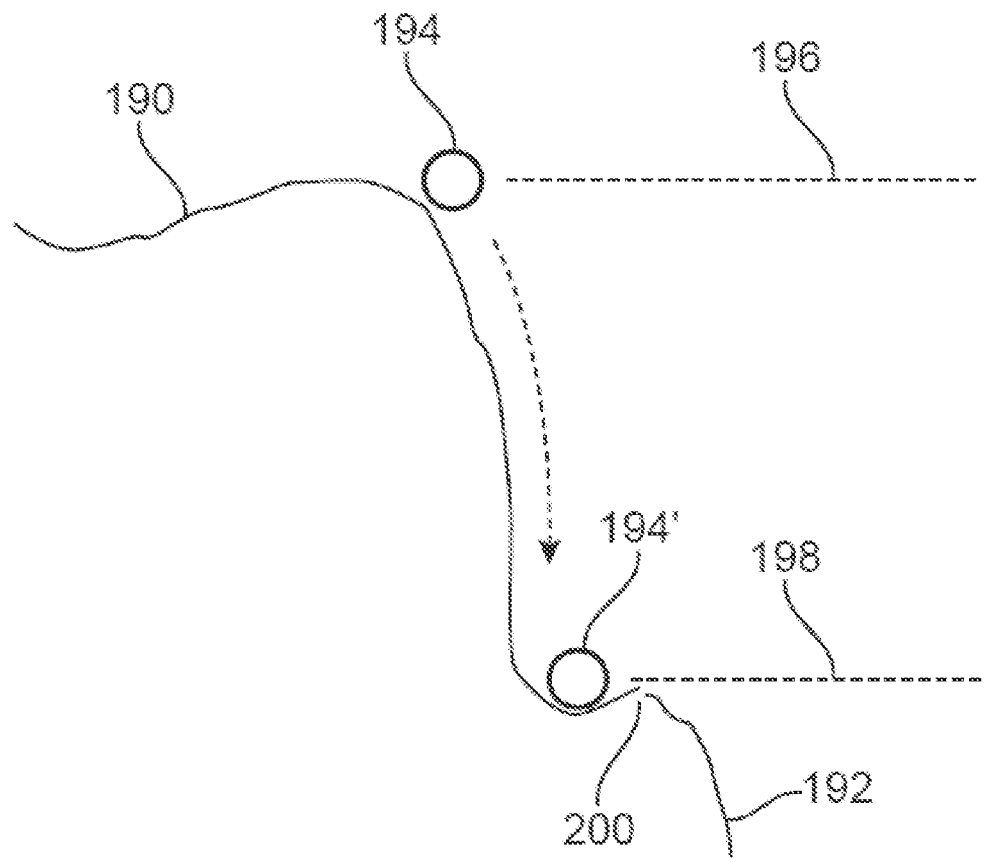
FIG. 4 shows a rolling or dropping ball method for detecting the tooth boundary during treatment planning.

Once the tooth labeled and a small set of mesh are identified, a drop ball algorithm may be used to detect the gum margin and teeth margin. FIG. 4 shows an exemplary process for digitally detecting and identifying a tooth boundary or geometry from the scanned dentition of the patient by simulating a rolling or dropping ball 194 to detect the boundary of the tooth 190 and gum 192. The ball 194 may be simulated to roll from a high energy state 196, e.g., at the tooth crown, to a low resting state 198, e.g., at bottom of the tooth. As the ball 194' rolls down longitude, there is a bump 200 which tip up at the margin area between the tooth and gum where the inflection changes. By looking at these areas and at the correct curvature changes, the margin line can be detected. This method can also detect occlusal teeth margins and gum margins as well.

Figure 5A:
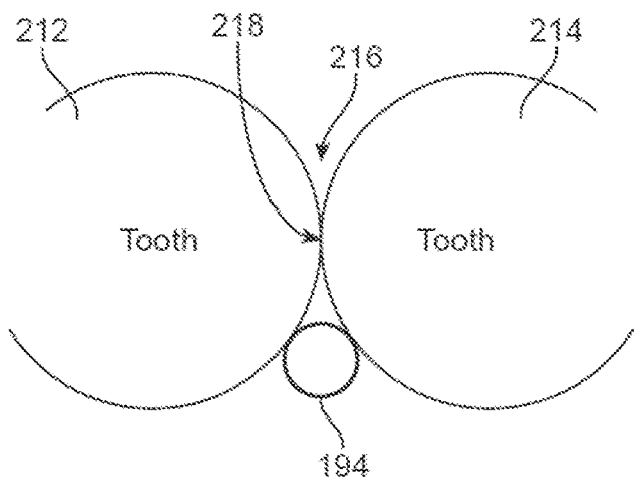
FIG. 5A shows how the rolling or dropping ball follows the clevis of teeth.
Figure 5B:
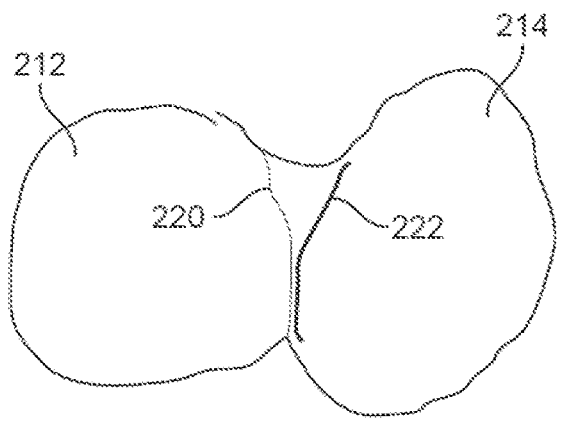
FIG. 5B shows how the ball trajectory path can be used to find the margin lines between adjacent teeth.

However, to detect the side margin between two adjacent teeth, the rolling ball algorithm may be used, as described, to follow the known margin lines of the teeth but in-between the adjacent teeth, the boundary of the teeth may be extrapolated. For instance, FIG. 5A shows an example where the rolling ball 194 may be rolled to follow the outline of adjacent teeth 212, 214. The region 218 in-between the teeth may be generally inaccessible to the ball 194 but the ball will naturally follow the clevis 216 of the teeth. Hence, the extrapolated trajectory path 220, 222 that the rolling ball 194 would follow between the teeth 212, 214 can be used to find the margin lines between adjacent teeth 212, 214 even though the ball 194 may not access the region 218 in-between, as illustrated in FIG. 5B.

Figure 5C:
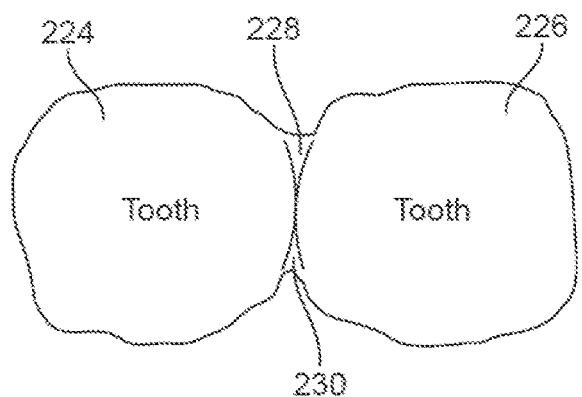
FIG. 5C show how once the margins are defined, the entire dental model may be separated into two portions to detect a tooth boundary or geometry.

As shown in FIG. 5C, once the margins are defined over the model, the entire dental model may be separated into two parts: a hard crown surface and a soft gum surface. In one embodiment, the "hard" surface 224, 226 may be considered a rigid surface which moves in an integral part and maintains its shape whiling moving. The "soft" surface 228, 230 may be attached to the "hard" surface 224, 226 and may deform based on the movements of the hard surface 224, 226. Such a movement does not change the overall topological structure of the dental model, hence the finished model by default is watertight, which fits a 3D printer requirement.

This deviates from the traditional separate model to individual tooth model, which requires models to be trimmed and then capped (hole filling) to make it watertight. Due to the complexity of scanned tooth geometry, such trim and hole filling is a very complex process.

Figure 6:
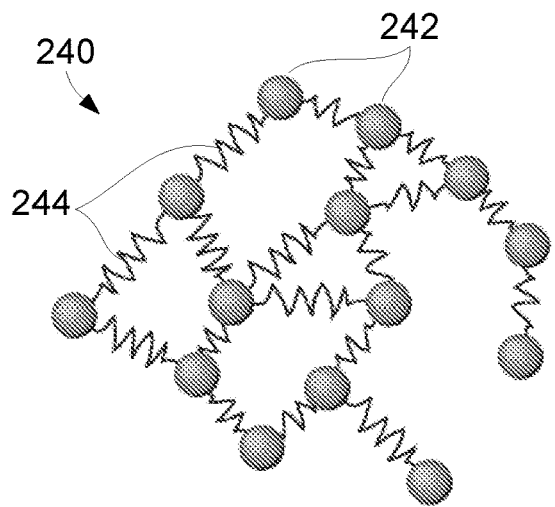
FIG. 6 shows an exemplary mass-spring model which may be used to model the teeth and gums as an interconnected system.
Figure 7:
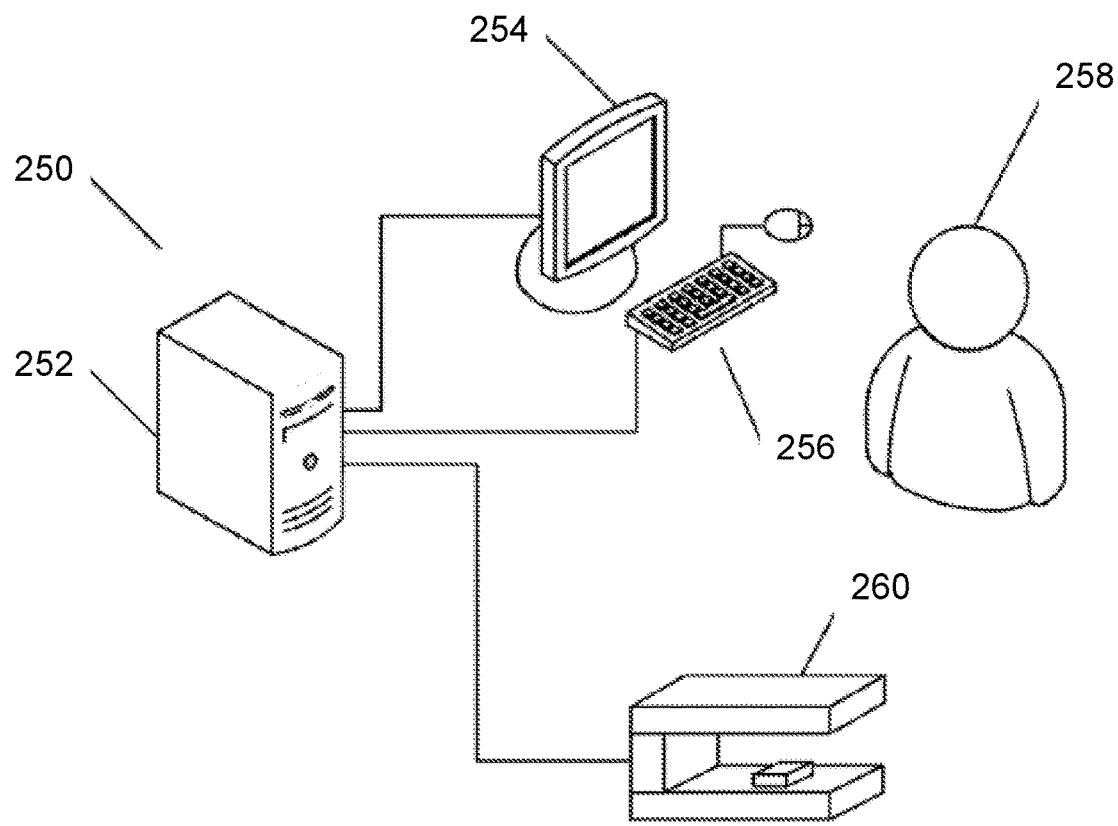
FIG. 7 shows an example of how the treatment planning may be implemented with respect to the patient.

FIG. 6 shows an exemplary mass-spring model 240 which may be applied to the dental model in determining tooth movement. It is generally desirable in some settings to synchronize the movement and operation of the individual tooth models to have a few tooth models operate in a choreographed manner as dictated by a treating professional. Having this choreographed movement is not typically possible through manual control where the tooth models move randomly and independently. The present control method and/or system are ideal for use in moving a number of tooth models and to provide synchronized tooth movement. Such a method may be non-swarming to avoid any collisions between the teeth and to also avoid the appearance of merely random movements, at least in some applications. Rather, it is desirable for the tooth models to each react safely to environmental conditions such as changes in bone structure and soft tissue during group tooth movement of choreographed tooth models.

The mass-spring model 240 may be constrained to be directly attached to a hard surface and the model 240 can be stretched or compressed. Any number of algorithms can be used to calculate its shape, e.g. mass-spring model, in one implementation of mass-spring model 240, two nodes may be modeled as mass points connected by a parallel circuit of a spring and a damper. In this approach, the body is modeled as a set of point masses (nodes) connected by ideal weightless elastic springs obeying some variant of Hooke's law. These nodes may either derive from the edges of a two-dimensional polygonal mesh representation of the surface of the object, or from a three-dimensional network of nodes and edges modeling the internal structure of the object (or even a one-dimensional system of links, if for example a rope or hair strand is being simulated). Additional springs between nodes can be added, or the force law of the springs modified, to achieve desired effects. Having the dental model constrained as a mass-spring model 240 helps to synchronize the movement and operation of the individual tooth models to have a few tooth models operate in a choreographed manner.

Applying Newton's second law to the point masses including the forces applied by the springs and any external forces (due to contact, gravity, etc.) gives a system of differential equations for the motion of the nodes, which is solved by standard numerical schemes for solving ordinary differential equations. Rendering of a three-dimensional mass-spring lattice is often done using free-form deformation, in which the rendered mesh is embedded in the lattice and distorted to conform to the shape of the lattice as it evolves. Assuming all point masses equal to zero, one can obtain the stretched grid method aimed at several engineering problems solution relative to the elastic grid behavior.

Another way to calculate the model 240 is using finite element analysis (FEA) models where the "soft" parts of the model are separated into smaller FEA elements, e.g., tetrahedron or cube elements, and some of the element surfaces may be attached to "hard" portions as so called boundary condition in FEA analysis while "soft" portions (gum portions) may be assigned various material properties such as Young's Modulus consistent with gum portions. While the hard parts are moving, the boundary condition may change and hence all the elements based on its connections to its neighboring elements may form a large matrices. By solving such matrices, each individual element shape and locations may be calculated to give a calculated gum deformation during treatment.

In one embodiment, the body may be modeled as a three-dimensional elastic continuum by breaking it into a large number of solid elements which fit together, and for which a model of the material may be solved for determining the stresses and strains in each element. The elements are typically tetrahedral, the nodes being the vertices of the tetrahedra (tetrahedralize a three dimensional region bounded by a polygon mesh into tetrahedra, similarly to how a two-dimensional polygon may be triangulated into triangles). The strain (which measures the local deformation of the points of the material from their rest state) may be quantified by the strain tensor. The stress (which measures the local forces per-unit area in all directions acting on the material) may be quantified by the Cauchy stress tensor. Given the current local strain, the local stress can be computed via the generalized form of Hooke's law. The equation of motion of the element nodes may be obtained by integrating the stress field over each element and relating this, via Newton's second law, to the node accelerations.

An energy minimization method can be used, which is motivated by variational principles and the physics of surfaces, which dictate that a constrained surface will assume the shape which minimizes the total energy of deformation (analogous to a soap bubble). Expressing the energy of a surface in terms of its local deformation (the energy is due to a combination of stretching and bending), the local force on the surface is given by differentiating the energy with respect to position, yielding an equation of motion which can be solved in the standard ways.

Shape matching can be used where penalty forces or constraints are applied to the model to drive it towards its original shape (e.g., the material behaves as if it has shape memory). To conserve momentum the rotation of the body must be estimated properly, for example via polar decomposition. To approximate finite element simulation, shape matching can be applied to three dimensional lattices and multiple shape matching constraints blended.

Deformation can also be handled by a traditional rigid-body physics engine, modeling the soft-body motion using a network of multiple rigid bodies connected by constraints, and using, for example, matrix-palette skinning to generate a surface mesh for rendering. This is the approach used for deformable objects in Havok Destruction.

The processes, computer readable medium and systems described herein may be performed on various types of hardware, such as computer systems 230. Such computer systems 230 may include a bus or other communication mechanism for communicating information and a processor coupled with the bus for processing information. A computer system 230 may have a main memory, such as a random access memory or other dynamic storage device, coupled to the bus. The main memory may be used to store instructions and temporary variables. The computer system 250 may also include it read-only memory or other static storage device coupled to the bus for storing static information and instructions.

The computer system 250 may also be coupled to a display, such as a CRT or LCD monitor 254. Input devices 256 may also be coupled to the computer system 250. These input devices 256 may include a mouse, a trackball, cursor direction keys, etc. for use by the user 258. Computer systems 250 described herein may include, but are not limited to, the computer 252, display 254, scanner/3D printer 260, and/or input devices 256. Each computer system 250 may be implemented using one or more physical computers or computer systems or portions thereof. The instructions executed by the computer system 250 may also be read in from a computer-readable medium. The computer-readable medium may be a CD, DVD, optical or magnetic disk, laserdisc, carrier wave, or any other medium that is readable by the computer system 250. In some embodiments, hardwired circuitry may be used in place of or in combination with software instructions executed by the processor.

As will be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described herein may be embodied in, and fully automated via, software code modules executed by one or more general purpose computers or processors, such as those computer systems described herein. The code modules may be stored in any type of computer-readable medium or other computer storage device. Some or all of the methods may alternatively be embodied in specialized computer hardware.

It should be emphasized that many variations and modifications may be made to the herein-described embodiments, the elements of which are to be understood as being among other acceptable examples. All such modifications and variations are intended to be included herein within the scope of this disclosure and protected by the following claims.

The applications of the devices and methods discussed above are not limited to the one described but may include any number of further treatment applications. Modification of the above-described assemblies and methods for carrying out the invention, combinations between different variations as practicable, and variations of aspects of the invention that are obvious to those of skill in the art are intended to be within the scope of the claims.

What is claimed is:

1. A computer-implemented method for planning a treatment for correcting malocclusions, comprising:
    receiving a scanned dental model of a subject's dentition;
    generating a digitized three-dimensional dental anatomy model by one or more processors;
    applying a label to one or more teeth within the digitized three-dimensional dental model;
    simulating a rolling ball process along an exterior of the one or more teeth and gums within the digitized three-dimensional dental model and detecting for changes in a path of the simulated rolling ball;
    determining a boundary between each of the one or more teeth and gums based on a path or trajectory of the rolling ball, wherein a change in energy state from a high energy state to a low resting state of the simulated rolling ball while detecting for inflection changes is indicative of the boundary between each of the one or more teeth and gums;
    extrapolating a further boundary between adjacent teeth which is inaccessible to the simulated rolling ball by projecting a trajectory of the rolling ball between the adjacent teeth;
    assigning a hard or soft region to each of the one or more teeth and gums within the digitized three-dimensional dental model;
    moving a position of the one or more teeth within the digitized three-dimensional dental model to correct for malocclusions; and
    generating an adjusted dental anatomy model in developing a treatment plan.

2. The method of claim 1 wherein receiving a scanned dental model comprises receiving a scanned image of the dentition or of an impression of the dentition.

3. The method of claim 1 wherein applying a label comprises receiving input from a user via a user interface in applying the label to the one or more teeth within the dental model.

4. The method of claim 1 wherein determining a boundary comprising determining a crown/gum margin.

5. The method of claim 1 wherein assigning a hard or soft region comprises assigning hard regions to the one or more teeth and soft regions to the gums.

6. The method of claim 1 wherein moving a position comprises applying a user-defined moving widget to one or more teeth.

7. The method of claim 6 wherein the moving widget comprises widgets for mesial/distal, lingual/facial, or vertical operations.

8. The method of claim 1 wherein moving a position comprises morphing a new dental model from the dental model.

9. The method of claim 8 wherein morphing comprises generating a model for a subsequent dental treatment stage.

10. The method of claim 1 further comprising fabricating one or more aligners to move the one or more teeth according to the treatment plan.

11. The method of claim 1 wherein each step occurs in a single visit by the subject to a dental office.

12. A computer-implemented method for planning a treatment for correcting malocclusions, comprising:
    scanning a subject's dentition to create a digitized three-dimensional dental model;
    applying a label to one or more teeth within the digitized three-dimensional dental model;
    rolling a simulated ball digitally along an exterior of the one or more teeth and gums within the digitized three-dimensional dental model and detecting for inflection changes in a path of the simulated rolling ball;
    determining a boundary between each of the one or more teeth and gums based on a path or trajectory of the simulated rolling ball, wherein a change in energy state from a high energy state to a low resting state along the path of the simulated rolling ball is indicative of the boundary between each of the one or more teeth and gums;

extrapolating a further boundary between adjacent teeth which is inaccessible to the simulated rolling ball by projecting a trajectory of the rolling ball between the adjacent teeth;

assigning a hard region to each of the one or more teeth and a soft region to gums within the digitized three-dimensional dental model moving a position of the one or more teeth within the digitized three-dimensional dental model to correct for malocclusions; and generating an updated digitized three-dimensional dental model in developing a treatment plan.

13. The method of claim 12 further comprising fabricating one or more aligners to move the one or more teeth according to the treatment plan.

14. The method of claim 13 wherein fabricating one or more aligners comprises 3D printing the one or more aligners.

15. The method of claim 12 wherein applying a label comprises receiving input from a user via a user interface in applying the label to the one or more teeth within the dental model.

16. The method of claim 12 wherein determining a boundary comprising determining a crown/gum margin.

17. The method of claim 12 wherein moving a position comprises applying a user-defined moving widget to one or more teeth.

18. The method of claim 17 wherein the moving widget comprises widgets for mesial/distal, lingual/facial, or vertical operations.

19. The method of claim 12 wherein moving a position comprises morphing a new dental model from the dental model.

20. The method of claim 19 wherein morphing comprises generating a model for a subsequent dental treatment stage.

21. The method of claim 12 wherein each step occurs in a single visit by the subject to a dental office.

22. The method of claim 10 wherein fabricating one or more aligners comprises 3D printing the one or more aligners.

* * * * *